US011406278B2

(12) United States Patent
Barley et al.

(10) Patent No.: US 11,406,278 B2
(45) Date of Patent: Aug. 9, 2022

(54) NON-RIGID-BODY MORPHING OF VESSEL IMAGE USING INTRAVASCULAR DEVICE SHAPE

(71) Applicant: KONINKLIJKE PHILIPS N.V., Eindhoven (NL)

(72) Inventors: Maya Ella Barley, Watford (GB); Adrien Emmanuel Desjardins, Waterloo (CA); Raymond Chan, San Diego (CA); Gert Wim 'T Hooft, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 142 days.

(21) Appl. No.: 16/752,763

(22) Filed: Jan. 27, 2020

(65) Prior Publication Data
US 2020/0163584 A1    May 28, 2020

Related U.S. Application Data (63) Continuation of application No. 14/000,415, filed as application No. PCT/IB2012/050623 on Feb. 13, 2012, now abandoned.
(Continued)

(51) Int. Cl.
*A61B 5/06* (2006.01)
*A61B 6/12* (2006.01)
(Continued)

(52) U.S. Cl.
CPC ............ *A61B 5/066* (2013.01); *A61B 5/0084* (2013.01); *A61B 5/055* (2013.01); *A61B 5/062* (2013.01);
(Continued)

(58) Field of Classification Search
CPC . A61B 34/20; A61B 34/25; A61B 2034/2046; A61B 2034/2051;
(Continued)

(56) References Cited

U.S. PATENT DOCUMENTS 6,317,621 B1   11/2001   Mann et al.
8,738,115 B2   5/2014   Amberg
(Continued)

FOREIGN PATENT DOCUMENTS

JP   0850128 A   2/1996
JP   3344835 B2   11/2002
(Continued)

OTHER PUBLICATIONS

Shape Tape https://www.electronic products.com/Optoelectronics/Distributed-measurement_tape_knows_its_exact_position.aspx, Dec. 1998).
(Continued)

*Primary Examiner* — Carolyn A Pehlke (57) ABSTRACT

A medical method and system include a medical imaging system configured to generate images of an interventional procedure. An overlay generator is configured to generate an overlay image on the images of the interventional procedure. An interventional device tracking system is configured to track a three-dimensional position, orientation and shape of the interventional device during the procedure, wherein the overlay image is dynamically updated in response to deformations caused to an organ of interest by the interventional device during the procedure.

18 Claims, 4 Drawing Sheets

Related U.S. Application Data (60) Provisional application No. 61/446,405, filed on Feb. 24, 2011.

(51) Int. Cl.

| | | |
|---|---|---|
| *A61B 5/00* | (2006.01) | |
| *A61B 34/20* | (2016.01) | |
| *A61B 5/055* | (2006.01) | |
| *A61B 8/08* | (2006.01) | |
| *A61B 90/00* | (2016.01) | |
| *A61B 6/00* | (2006.01) | |
| *A61B 17/00* | (2006.01) | |
| *A61B 6/03* | (2006.01) | |

(52) U.S. Cl.
CPC ............ *A61B 5/064* (2013.01); *A61B 5/6876* (2013.01); *A61B 5/742* (2013.01); *A61B 6/12* (2013.01); *A61B 6/463* (2013.01); *A61B 6/466* (2013.01); *A61B 6/485* (2013.01); *A61B 6/487* (2013.01); *A61B 6/5229* (2013.01); *A61B 8/0841* (2013.01); *A61B 34/20* (2016.02); *A61B 6/03* (2013.01); *A61B 6/504* (2013.01); *A61B 2017/00694* (2013.01); *A61B 2034/2051* (2016.02); *A61B 2034/2061* (2016.02); *A61B 2090/065* (2016.02); *A61B 2090/376* (2016.02)

(58) Field of Classification Search
CPC .... A61B 2034/2055; A61B 2034/2061; A61B 2034/2065; A61B 2034/2074; A61B 90/37
See application file for complete search history.

(56) References Cited

U.S. PATENT DOCUMENTS

| | | |
|---|---|---|
| 2005/0182319 A1 | 8/2005 | Glossop |
| 2006/0058643 A1 | 3/2006 | Florent et al. |
| 2007/0167738 A1 | 7/2007 | Timinger et al. |
| 2008/0123927 A1 | 5/2008 | Miga et al. |
| 2008/0147086 A1 | 6/2008 | Pfister et al. |
| 2009/0030306 A1 | 1/2009 | Miyoshi |
| 2009/0088628 A1 | 4/2009 | Klingenbeck-Regn |
| 2009/0088629 A1 | 4/2009 | Groszmann |
| 2009/0137952 A1 | 5/2009 | Ramamurthy et al. |
| 2009/0216114 A1 | 8/2009 | Gorges et al. |
| 2009/0226069 A1 | 9/2009 | Razzaque et al. |
| 2010/0030063 A1 | 2/2010 | Lee et al. |
| 2010/0121190 A1 | 5/2010 | Pagoulatos et al. |
| 2010/0169815 A1 | 7/2010 | Zhao et al. |
| 2010/0249507 A1 | 9/2010 | Prisco |
| 2010/0312096 A1 | 12/2010 | Guttman |
| 2011/0160571 A1* | 6/2011 | Cohen ............... A61B 5/066 600/424 |
| 2013/0211531 A1 | 8/2013 | Steines et al. |

FOREIGN PATENT DOCUMENTS

| | | |
|---|---|---|
| WO | 2009144730 | 12/2009 |
| WO | 2009153723 | 12/2009 |
| WO | 2010150147 | 12/2010 |

OTHER PUBLICATIONS

Teber, Dogu et al: "Augmented Reality: A New Tool to Improve Surgical Accuracy During Laparoscopic Partial Nephrectomy? Preliminary in Vitro and in Vivo Results"; European Urology 56.2 (2009):332-338.

McInerney et al: "Deformable Models in Medical Image Analysis: A Survey"; Medical Image Analysis 1.2 (1996):91-108.

Szekely et al: "Segmentation of 2_d and 3-D Objects From MRI Volume Data Using Constrained Elastic Deformation of Flexible Fourier Contour and Surface Models" Medical Image Analysis (1996), vol. 1, No. 1, pp. 19-34.

Neshat et al: "Real-Time Parametric Curved Needle Segmentation in 3D Ultrasound Images" Proc. IEEE EMBS International Conference on Biomedical Robotics and Biomechatronics, Scottsdale, AZ, Oct. 19-22, 2008, pp. 670-675.

\* cited by examiner

NON-RIGID-BODY MORPHING OF VESSEL IMAGE USING INTRAVASCULAR DEVICE SHAPE

CROSS-REFERENCE TO PRIOR APPLICATIONS

This application is a continuation of U.S. patent application Ser. No. 14/000,415, filed on Aug. 20, 2013 which is a National Stage of International Application No. PCT/IB2012/050623 filed on Feb. 13, 2012 which claims benefit of Provisional No. 61/446,105 filed on Feb. 24, 2011, all of which are incorporated herein in whole by reference.

This disclosure relates to image registration, and more particularly to dynamic overlay morphing in accordance with dynamic behavior of internal organs, endoluminal anatomy, or vascular structures due to interventional medical devices.

Stand-alone fluoroscopy is a standard imaging modality for many interventional procedures. One significant drawback to x-ray usage is the lack of soft-tissue definition. While interventional devices are clearly visible, the treatment site (typically a soft tissue structure) is almost invisible unless some form of x-ray contrast agent is used to define it more clearly. Furthermore, such contrast agents are frequently nephrotoxic, and their use needs to be minimized. As a result, three-dimensional (3D) image overlay on live fluoroscopy would be desirable in many x-ray guided interventional procedures. The overlay would assist in the guidance of an interventional device to the treatment site by providing continuously-visualized, static, morphological information. The 3D overlay must accurately reflect the real anatomy (to within a few mm) to be clinically relevant, which is often a challenging task.

The 3D overlaid image may be either an intra-procedurally-generated image (such as a Philips® 3D-RA™ or XperCT™) or a pre-procedural image (e.g., magnetic resonance (MR) or computed tomography (CT)). The image is intended to closely correspond to the patient's anatomy for the duration of time that it is used as an overlay. However, it is widely known that a stiff instrument can significantly deform a vessel's shape by pressing against its walls.

Although interventional devices are inside the patient's vessels, their trajectories on a fluoroscopic image may lie, in part, outside the static 3D overlay due to deformation of the real anatomy by the instruments. As a result, pre-procedural image overlays may not be accurate or clinically useful for guiding an interventional device into or through narrow lumens (e.g., a small vascular sidebranch).

Multiple technologies for 3D localization and sensing along an interventional device include the following. Electromagnetic (EM) localization where single-point EM sensors can be used to accurately localize points at intervals along an interventional device. By interpolating between these points, the 3D device shape can be determined. Fiber-optic shape sensing based on scattering from Fiber Bragg Gratings (FBG) or Rayleigh scattering is another approach that permits the entire device shape in three dimensions to be determined. X-ray-based 3D device shape determination may also be used to interrogate the 3D shape of an interventional device from x-ray alone, using a combination of known device-based x-ray markers and x-ray system geometry to estimate location and configuration of the interventional device. Given any particular imaging system geometry, the shapes of these markers on an x-ray image could vary depending on their 3D orientations, which depend, in turn, on the interventional device shapes. Therefore, x-ray markers may be used to approximate the 3D device shape. Characteristics of the device shape may also be determined with other sensing schemes occurring simultaneously with fluoroscopy, such as with ultrasound (conventional imaging or ultrasound time-of-flight localization of beacons embedded within the device), photoacoustics, impedance-based localization, etc.

U.S. Patent Application Publication No. US2005/0182319 A1 to Glossop discloses a system for registering, verifying, dynamically referencing, and navigating an anatomical region of interest of a patient. The anatomical region of interest is imaged using an imaging via an x-ray device. A tracked registration device is removably inserted into a conduit within the anatomical region and the position of the registration device is sampled by a tracking device as the registration device is moved within the anatomical region through the catheter. The sampled position data is registered to the image data to register the path of the conduit to the anatomical region of interest. The same device is used to dynamically reference the movements affecting the anatomical region and modify the registration in real time.

In accordance with the present principles, a medical method and system include a medical imaging system configured to generate images of an interventional procedure. An overlay generator is configured to generate an overlay image on the images of the interventional procedure. An interventional device tracking system is configured to track a 3D position, orientation and shape of the interventional device during the procedure, wherein the overlay image is dynamically updated in response to deformations caused to an organ of interest by the interventional device during the procedure.

A method for a medical procedure includes generating images of an interventional procedure; generating an overlay image on the images of the interventional procedure; tracking a position, orientation and shape of the interventional device during the procedure; dynamically updating the overlay image in response to deformations caused to an organ of interest by the interventional device during the procedure.

Another method for a medical procedure includes generating images of an interventional procedure; generating an overlay image on the images of the interventional procedure; tracking a position, orientation and shape of the interventional device during the procedure; checking whether the interventional device remains within a boundary of the overlay image; if the interventional device is not fully enclosed in the boundary, determining a deformation of the organ that will permit the interventional device to remain within the boundary; and dynamically updating the overlay image in accordance with the deformation.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

The present disclosure describes three-dimensional (3D) image overlay systems and methods. The present embodiments improve accuracy of 3D image overlays on live fluoroscopy images for interventional procedures by non-rigid-body warping of the 3D image of an organ based on the 3D shape of the interventional device within that organ. This technique could be applied in any (e.g., minimally-invasive) interventional vascular, luminal or interstitial procedure where highly precise device placement is needed and/or the tissue morphology (e.g., the vessel in a vascular procedure) is significantly affected by inserting a rigid or semi-rigid device (e.g., abdominal or thoracic aorta stent-grafting, carotid artery stenting, Uterine fibroid embolizations (UFEs), Transjugular Intrahepatic Portosystemic Shunt (TIPS), Transarterial Chemoembolization (TACE) procedures), etc. The present embodiments may be employed in any interventional vascular procedures, e.g., where highly precise device-placement is needed and/or the vessel morphology is significantly affected by inserting a comparatively stiff device.

It also should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Figure 1:
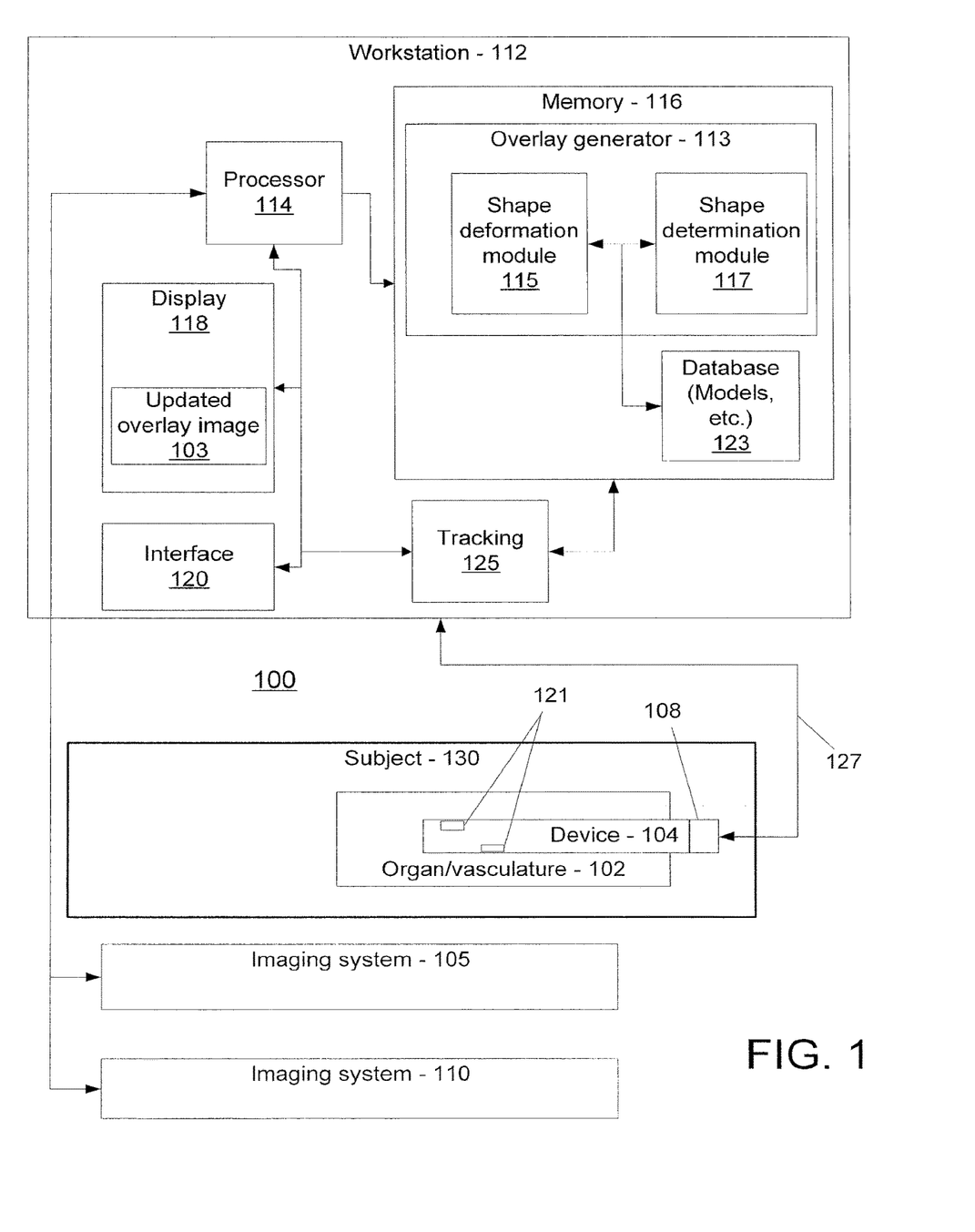
FIG. 1 is a block/flow diagram showing a system/method for updating an overlay image in accordance with the present principles.

Referring now to the drawings in which like numerals represent the same or similar elements and initially to FIG. 1, a system 100 for maintaining registration between a fluoroscopy image and an overlay is illustratively depicted. The system 100 improves the accuracy of a 3D image overlay on a live imaging (e.g., fluoroscopy) system or platform 105 for vascular interventional procedures. In one embodiment, imaging system 105 includes a fluoroscopy system which may be employed without the use of contrast dyes as a result of the dynamic overlay in accordance with the present principles.

The system 100 includes an interventional device 104 intended for insertion into vascular structures. The interventional device 104 may include a catheter, a probe, a diagnostic sensor, a guidewire, a therapy delivering element, a needle for biopsy or therapy delivery (e.g. injection of biologics, ablative, or embolic material), a cutting device, a shaping device, a prosthetic support device, an endoscope, a robot, an electrode, a filter device, a balloon device or any other rigid, semi-rigid or fully flexible instrument. The interventional device 104 may be coupled to a workstation or other console 112 by a cable 127 or other connection. A procedure is supervised and/or managed from the workstation or console 112. Workstation 112 preferably includes one or more processors 114 and memory 116 for storing programs and applications.

Memory 116 includes an overlay generator 113. Overlay generator 113 may include a shape deformation module 115 configured to interpret feedback signals from device 104 and determine a new shape for an organ or vasculature 102 affected by the device 104 during a procedure. The shape deformation module 115 accepts as input a set of parameters describing how an image space is deformed, and produces as output a deformed 3D anatomical image of the vasculature 102. Overlay generator 113 also includes or receives input from a shape determination module 117 for determining a 3D shape of the interventional device(s) 104 and a position(s) of the device 104 in image space. The module 117 may also measure or track other parameters such as pressure, strain, shear, or proximity/contact sensors 121 on the device 104 to provide additional feedback measurements.

Modules 115 and 117 work together to provide updated 3D overlay images which are consistent with a shape and position of the device 104 as it is moved into or through a vasculature. There is a data connection between modules 115 and 117 that permits an estimate of the 3D shape(s) of the interventional device(s) 104 to be used to determine the set of parameters provided as input to the shape deformation module 115. The parameters are chosen so that the vascular structures in a deformed 3D anatomical image 103 are consistent with the estimated shape of the interventional device 104.

A database 123 is stored in memory or is accessible over a network and includes historic data, models, and/or finite element representations of organs and their deformation response to particular instruments for particular procedures. The database 123 may be employed by either or both modules 115 and 117 to update the 3D images for a dynamic overlay.

In one embodiment, pressure or other sensors 121 may be mounted on the device 104 so that pressure or other measurements can be taken and recorded. Other instrumentality 108 such as, e.g., optical fiber sensing (Fiber Bragg gratings (FBG), Rayleigh scattering optical fiber, etc.), EM tracking or other device localization/configuration determining capability may be employed to further determine a position and shape of the device 104. Since the position and shape of the device 104 is known, the pressure measurements, etc. provide additional information about the device 104 interacting with the vasculature 102. A determination of tissue that is displaced as a result of the device 104 may be computed by shape deformation module 115. Shape deformation module 115 is configured to use any other feedback from device 104 to reconstruct 3D deformations, deflections and other changes associated with a medical device or instrument 104 and/or its surrounding region. Device tracking 125 is employed to estimate non-rigid body morphing of a 3D image (from pre-procedural imaging or intra-procedural 3D treatment, ultrasound, etc.). The morphing is computed such that the morphed 3D image 103 more accurately reflects a real-time vascular anatomy.

Workstation 112 may include a display 118 for viewing internal images of a subject 130. In addition to the fluoroscopy or other real-time imaging platform 105, an imaging system 110 may optionally be provided. Imaging system 110 may include a magnetic resonance imaging (MRI) system, a computed tomography (CT) system, an ultrasound system, a nuclear imaging system or any other system configured to generate 3D images of the subject 130. The system 100 may or may not include such an imaging system 110 as images may be taken a priori and sent to the workstation 112 over a network or transferred to the workstation via a memory storage device.

Display or displays 118 may be employed to render fluoroscopy or other real-time images and 3D overlays (from images previously taken of the subject 130). The 3D overlay images include the vasculature through which the interventional device(s) 104 is/are guided. Display 118 also permits a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

System 100 may include a 3D tracking technology 125, such as EM tracking, optical shape sensing or a similar 3D position or orientation sensing system which may be integrated with the workstation 112 or be a separate system. An EM tracking system 125 includes an EM sensing module used to interpret EM signals generated by the medical device 104 during a procedure. The medical device 104 may include one or more EM tracking sensors, which may be mounted on the device 104. The medical device 104 may also include a fiber optic shape sensing device (125) which provides optical readings that are reconstructed into information about device location, orientation, and shape.

Workstation 112 may include an optical interrogation unit or module (125), which is employed to transmit light and detect light returning from all fibers if optical fiber sensing is employed. This permits the determination of strains or other parameters, which will be used to interpret the shape, orientation, or other characteristics, sensed by the interventional device 104. The light signals will be employed as feedback to understand the device 104 to tissue interaction in the subject 130. The shape determination module 117 and the shape deformation module 115 are employed to compute a new overlay image that accounts for deformations due to device—tissue interactions. This improves the accuracy of the overlay 103 making the image closer to an actual organ shape during a procedure.

Figure 2:
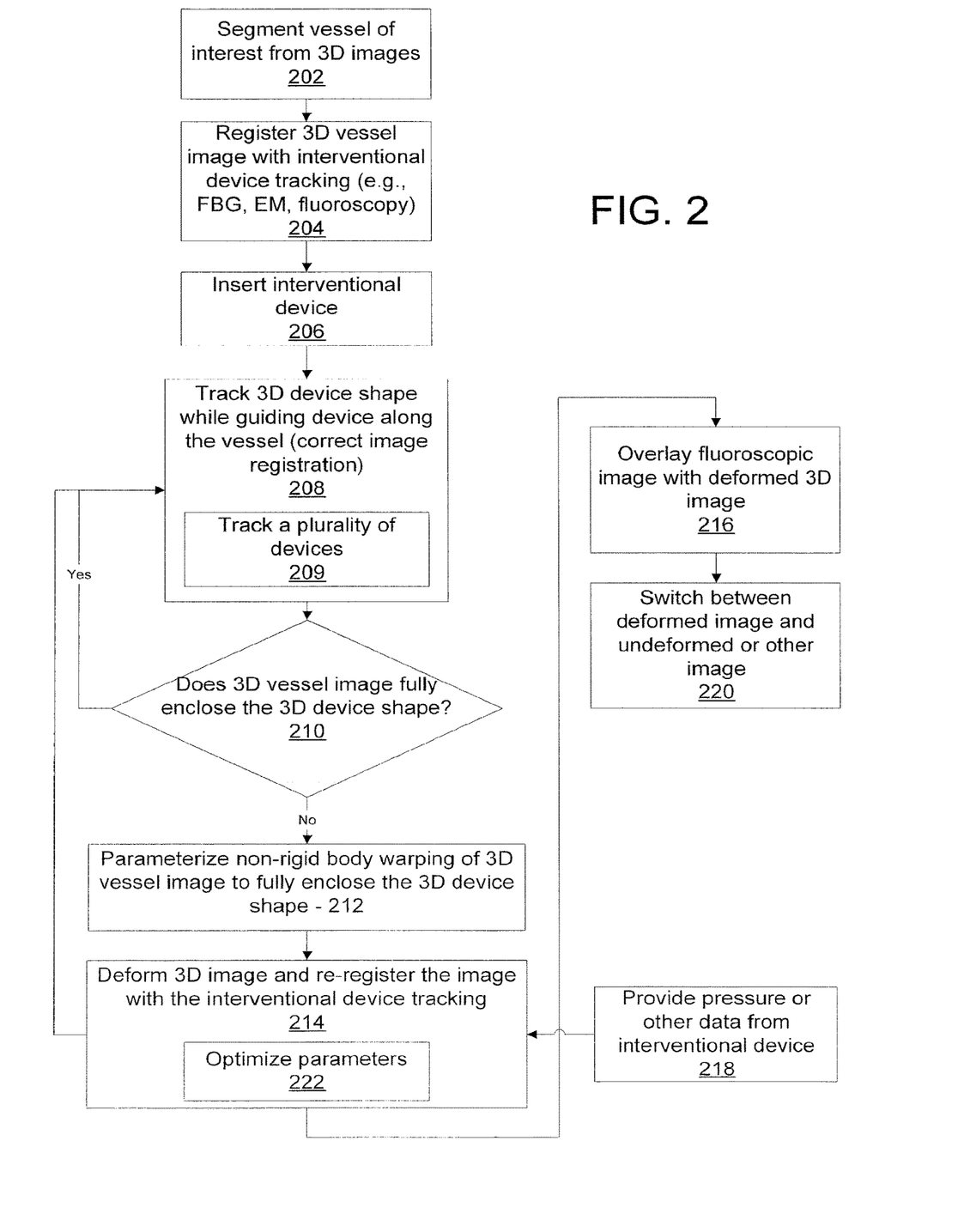
FIG. 2 is a flow diagram showing a method for performing a procedure with updated overlay images in accordance with one illustrative embodiment.

Referring to FIG. 2, a block/flow diagram is shown for updating a three-dimensional overlay in accordance with tissue morphing as a result of a medical device for one illustrative embodiment. In block 202, 3D vessel imaging and segmentation of vessels of interest is performed. Image acquisition and segmentation of vessels from such images may be performed using known techniques. In block 204, a 3D shape of the interventional device is determined, for example, by EM localization of one or more points along the interventional device, optical shape sensing (using optical interrogation of fiber strains and 3D reconstruction of strain fields to track the continuous device shape in three dimensions) or x-ray-based 3D device shape sensing (e.g., using 3D markers at intervals along the device). The registration of 3D images to tracking technologies may employ known techniques. In block 206, a clinician guides an interventional device into or through a vessel of interest.

In block 208, the 3D shape of the device is tracked while guiding the device along a vasculature. The 3D shape of the interventional device determined using the tracking technology should lie within the vessel boundaries displayed in the 3D vessel image. This is checked in block 210.

In block 209, in one embodiment, the shapes of multiple interventional devices may be tracked and a parameterization method in block 212 would involve determining the anatomy with a 3D vessel shape that optimally encompasses the shape of all the 3D devices, based on both the available measurements and the accumulated prior knowledge available about the procedure and device(s) of interest.

In block 210, the device should be physically contained by walls of the vessel. Therefore, if the 3D vessel image is a true representation of the real-time patient anatomy, the device tracking technology and 3D imaging space are accurately co-registered, and the device remains within the vasculature.

If this is not the case, this could be due to patient or table movement. This causes a translation of the 3D image and device tracking space, which needs to be accounted for. Another misregistration may be due to respiratory or cardiac movement. This may cause a cyclical movement of vessels that are within the patient's thorax or proximal to the diaphragm. There are many vessels whose morphologies are not affected by the respiratory or cardiac cycles (e.g. abdominal aorta, limb arteries, neuro vessels etc.). These cases may be accounted for in rigid body movement and/or cyclic compensation algorithms.

Another misregistration may be from the device causing vessel deformation. Non-rigid-body warping of the 3D image is needed to update the 3D image so that it better reflects the real-time anatomy of the patient in accordance with the present principles.

In block 212, the non-rigid-body deformation of the 3D image is parameterized so that it more accurately reflects the patient's real-time anatomy. This may be achieved in multiple ways.

In block 214, one example of non-rigid-body warping is to assume that the 3D anatomy enclosing the vessel has deformed so that the vessel can continue to enclose the tracked 3D shape of the interventional device, and that the vessel diameter/length remains constant. The parameterization method then involves determining the anatomy with a 3D vessel shape that encompasses the 3D device shape. After the 3D image is deformed, it is reregistered with the device by returning to block 208, if needed.

More advanced examples may permit for the deformation of both the 3D anatomy enclosing the vessel and the vessel diameter/length. In these examples, it would be useful to include vessel characteristics such as longitudinal and radial vessel elasticities and an estimate of vessel deformability in that anatomical area (which is affected, for example, by the degree of vessel calcification—seen on CT and fluoroscopy—and the number of spinal arteries). Characteristics of the 3D image would therefore be useful to determine what types of deformations should be applied.

In block 222, in one embodiment, optimal parameters utilized for deformation of the 3D image may optionally be determined by taking into account parameters obtained at previous time points. With assumptions about continuity of the anatomical deformations in time, the space of parameters that is considered could be significantly constrained, which could in turn lead to faster processing times and/or predictable deformations. Parameter optimization may rely on other data as well.

For example, in block 218, one embodiment provides pressure or other parametric sensing along the interventional device (either at distinct points or continuously along a segment as could be provided by FBGs, for example). This provides new information on which points/segments of the interventional device are in contact with the vessel wall and which points/segments are floating freely within the lumen of the vessel. This also provides valuable information on the true vessel shape that can be employed to improve the non-rigid-body parameterization process.

In block 216, the fluoroscopic or real-time image is overlaid with the deformed 3D image.

In block 220, in one embodiment, a user/clinician is provided with a capability of switching back and forth between the warped 3D image and a non-warped 3D image via an interface (120, FIG. 1). By comparing the two images, the clinician can assess how much pressure is being applied to the vessel walls (and whether this pressure could be dangerous and lead to potential vessel rupture). Elastographic measurements could also be obtained automatically by analyzing the deformations obtained for the 3D images.

The process is updated throughout a procedure. This provides an updated and accurate overlay during the procedure.

Figure 3:
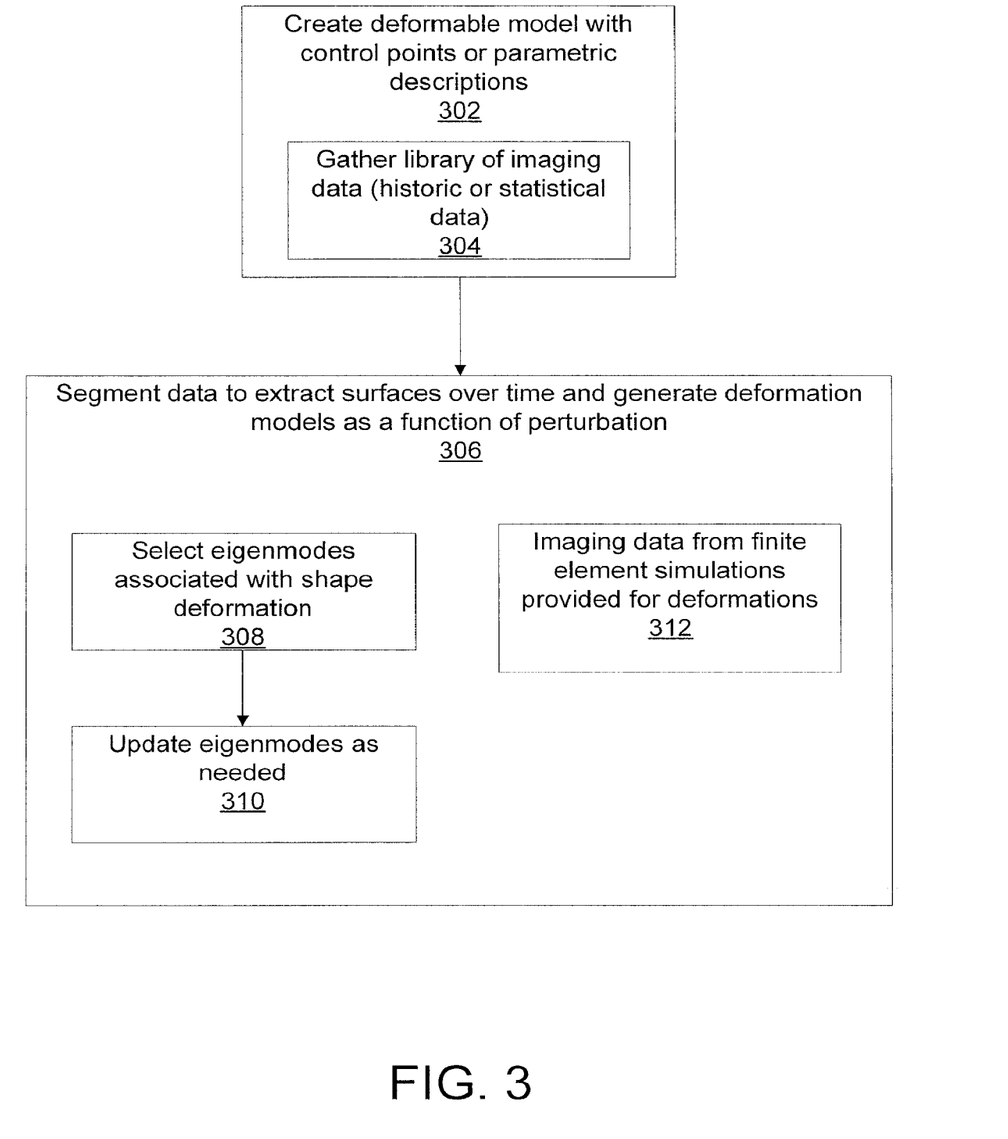
FIG. 3 is a flow diagram showing a method for updating an overlay image using models in accordance with another illustrative embodiment.

Referring to FIG. 3, another embodiment employs statistical or historic data to deform vessel images in accordance with the present principles. In block 302, a derivation of an anatomically-realistic deformable model is created with a minimal set of control points or parametric descriptions. A sparse set of tracked landmarks (localized in 3D by EM, impedance, acoustic, optical sensing, etc.) is available from the device and delivery assembly (e.g., a catheter or sheath) for adapting the rigid-body pose and deformation of the model. In block 304, one way of building this model includes gathering a library of imaging data acquired during an intervention (e.g., historic or statistical data). The data shows dynamic behavior of the anatomy as the instrumentation is moved within it.

In block 306, segmentation of the data can be performed to extract 3D surfaces evolving over time, and deformation models of the surface shape change as a function of perturbation are generated. In particular, a principal component analysis (or similar analytical methods for decomposition of shapes into component modes) may be employed to determine eigenmodes of shape deformation and associated eigenvalues which reflect the relative importance of each shape eigenvector. In block 308, a subset of eigenmodes associated with the largest eigenvalues can be selected to minimize the parameter space associated with shape deformation, while ensuring that the dominant deformation behaviors are still captured within the parametric model. Adaptation of the library-derived models to a particular patient anatomy (from 3D preprocedural data segmentation) and particular set of tracked feature points on the device can then occur by estimating the eigenmode coefficients/weighting values which minimize a distance metric computed between the model and observed measurements.

In block 310, the eigenmodes are updated as needed during the procedure to ensure that the model follows closely the deflection of the tissue as a result of the medical instrument. In this way, a more clinically meaningful display of tissue response may be projected in an overlay image, in particular, during a fluoroscopically tracked procedure. Other information about deformation functions of the anatomy of interest may be derived from vector velocity fields of pre-procedural phase-contrast MR imaging or tissue speckle tracking with ultrasound imaging. These other sources of measurement information can augment the prior knowledge available from libraries of segmented 3D surface models.

In addition to or instead of computing eigenmodes, a library of imaging data from actual studies may be substituted by a library of deformations that can be derived from finite element simulations of the anatomy deforming under instrument manipulation, in block 312. A host of potential libraries and training datasets for computing appropriate models for a range of different clinical interventions and instrumentation can be generated to broaden the scope of applicability.

Figure 4:
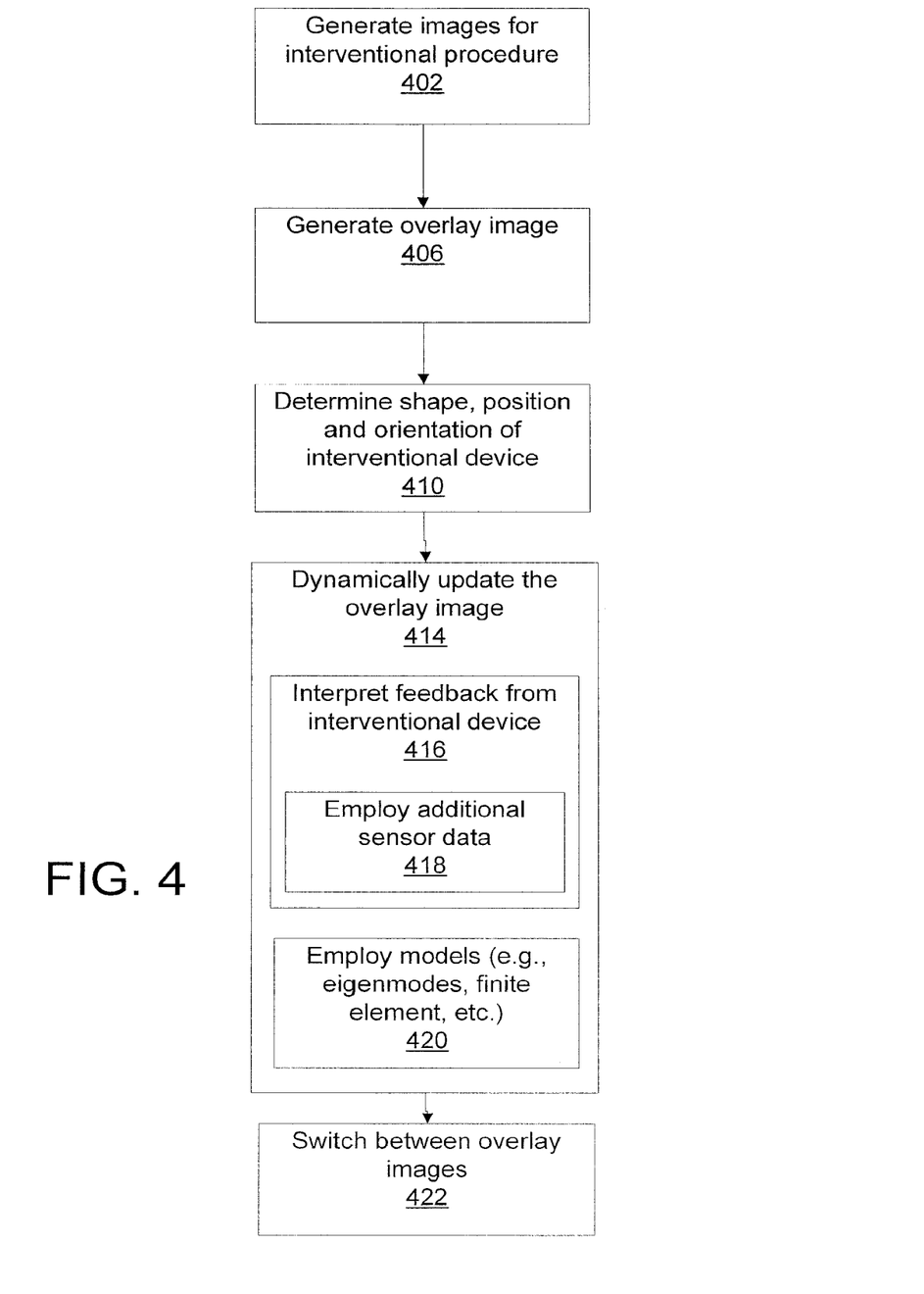
FIG. 4 is a flow diagram showing a method for updating an overlay image in accordance with another illustrative embodiment.

Referring to FIG. 4, a medical procedure is illustratively shown in accordance with another embodiment. In block 402, images of an interventional procedure are generated. These images are preferably real-time images generated using fluoroscopic imaging. In block 406, an overlay image is generated on the images of the interventional procedure. The overlay images preferably include three-dimensional anatomical images of a subject taken by, e.g., computed tomography, magnetic resonance imaging or other imaging methods.

In block 410, a position, orientation and shape of the interventional device (in 3D) are tracked during the procedure. The tracking may include using one or more of electromagnetic tracking, optical sensing, fluoroscopy marker tracking, etc.

In block 414, the overlay image is dynamically updated in response to 3D deformations caused to an organ of interest by the interventional device during the procedure. Updating the overlay image preferably includes interpreting feedback signals from the interventional device and determining a new shape for the organ affected by the interventional device in block 416. In block 418, the interventional device may include pressure sensors or other sensors, and measurements (e.g., pressures) may be employed to determine a deformation response of the organ.

In block 420, models of deformation responses of the organ may be stored and employed to update the overlay image of the organ. The models may generated by computing eigenmodes of tissue response, generated in accordance with finite element simulations or employ historic or statistical data to reproduce or predict organ movement. In block 422, a capability is provided to enable switching between the overlay image and an updated overlay image during the interventional procedure. In this way, the updated overlay can be compared with a previous or original overlay image.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for non-rigid-body morphing of vessel image using intravascular device shape (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical system, comprising:
a medical imaging device configured to generate images of an interventional procedure;
an overlay generating processor configured to generate an overlay image on the images of the interventional procedure, wherein the overlay image includes a three-dimensional (3D) anatomical image of an organ of interest; and
an interventional device tracking device configured to dynamically track a three dimensional (3D) position, orientation and shape of an interventional device during the interventional procedure;
wherein the overlay image is dynamically updated in response to deformations caused to the organ of interest by the interventional device during the interventional procedure, said deformations being determined based on real-time feedback received during the interventional procedure from a plurality of sensors situated along the interventional device that are configured to sense pressure, proximity, or contact along the interventional device.

2. The medical system as claimed in claim 1, wherein the overlay generating processor includes a shape deformation processor configured to interpret feedback signals from the interventional device and determine a new shape for the organ of interest affected by the interventional device.

3. The medical system as claimed in claim 1, wherein the overlay generating processor includes a shape determination processor for determining the position, the orientation and the shape of the interventional device in image space.

4. The medical system as claimed in claim 1, wherein the interventional device includes at least one of pressure, strain, shear, proximity, or contact sensors and sensor measurements that are employed to determine the deformations of the organ of interest.

5. The medical system as claimed in claim 1, further comprising a database configured to store models of deformation responses of the organ of interest which are employed by the overlay generating processor to update the overlay image of the organ of interest.

6. The medical system as claimed in claim 5, wherein the database stores at least one of eigenmodes of tissue response or finite element simulations.

7. The medical system as claimed in claim 1, wherein the interventional device tracking device includes at least one of electromagnetic tracking, optical sensing, or fluoroscopy marker tracking.

8. The medical system as claimed in claim 1, wherein the overlay image is taken by at least one of computed tomography, magnetic resonance imaging, ultrasound or nuclear imaging.

9. A non-transitory computer readable medium having stored thereon instructions which, when executed by processing circuitry, cause the processing circuitry to:
generate images of an interventional procedure;
generate an overlay image on the images of the interventional procedure, wherein the overlay image includes a 3D anatomical image of an organ of interest;
track a 3D position, orientation and shape of an interventional device during the interventional procedure; and
dynamically update the overlay image in response to deformations caused to the organ of interest by the interventional device during the interventional procedure, said deformations being determined based on real-time feedback received during the interventional procedure from a plurality of sensors situated along the interventional device that are configured to sense pressure, proximity, or contact along the interventional device.

10. The non-transitory computer readable medium as claimed in claim 9, wherein updating the overlay image includes interpreting feedback signals from the interventional device, and determining a new shape for the organ of interest affected by the interventional device.

11. The non-transitory computer readable medium as claimed in claim 9, further causing the processing circuitry to store models of deformation responses of the organ of interest which are employed to update the overlay image of the organ of interest.

12. The non-transitory computer readable medium as claimed in claim 11, wherein the models are generated by computing eigenmodes of tissue response.

13. The non-transitory computer readable medium as claimed in claim 11, wherein the models are generated in accordance with finite element simulations.

14. The non-transitory computer readable medium as claimed in claim 9, further comprising code that when executed by the processing circuitry causes processing circuitry to:
check whether the interventional device remains within a boundary of the overlay image; and
if the interventional device is not fully enclosed in the boundary, determine a deformation of the organ of interest that will permit the interventional device to remain within the boundary; and wherein dynamically updating includes dynamically updating the overlay image in accordance with the deformation.

15. The medical system as claimed in claim 1, wherein the overlay image is dynamically updated in response to deformations caused to a vessel enclosed by the organ of interest, and wherein the overlay generating processor is configured to determine a deformation of the 3D anatomical image based at least in part on elasticity characteristics of the vessel.

16. The medical system as claimed in claim 1, wherein the feedback comprises pressure sensing along the interventional device along a plurality of points of the interventional device, and wherein the overlay generating processor is configured to determine a deformation of the 3D anatomical image based at least in part on a determination of which points of the plurality of points are in contact with a vessel wall of the organ of interest.

17. The non-transitory computer readable medium of claim 9, wherein the overlay image is dynamically updated in response to deformations caused to a vessel enclosed by the organ of interest, and further comprising code that when executed by the processing circuitry cause the processing circuitry to determine a deformation of the 3D anatomical image based at least in part on elasticity characteristics of the vessel.

18. The non-transitory computer readable medium of claim 9, wherein the feedback comprises pressure sensing along the interventional device along a plurality of points of the interventional device, and further comprising code that when executed by the processing circuitry cause the processing circuitry to determine a deformation of the 3D anatomical image based at least in part on a determination of which points of the plurality of points are in contact with a vessel wall of the organ of interest.

* * * * *